United States Patent [19]

Steiner et al.

[11] Patent Number: 4,877,807
[45] Date of Patent: Oct. 31, 1989

[54] 5-PHENYL-1,2,3A,4,5,9B-HEXAHYDRO-3H-BENZ(E)INDOTES PREPARATION AND USE THEREOF AS DRUGS

[75] Inventors: Gerd Steiner, Kirchheim; Walter Himmele, Walldorf; Ernst Buschmann, Ludwigshafen; Hans-Juergen Teschendorf, Dudenhofen; Harald Weifenbach, Ludwigshafen, all of Fed. Rep. of Germany

[73] Assignee: BASF Aktiengesellschaft, Ludwigshafen, Fed. Rep. of Germany

[21] Appl. No.: 197,274

[22] Filed: May 23, 1988

[30] Foreign Application Priority Data

May 23, 1987 [DE] Fed. Rep. of Germany ....... 3717395

[51] Int. Cl.4 .................... A61K 31/40; C07D 209/60; C07D 207/06; C07D 207/08
[52] U.S. Cl. .................................. 514/411; 548/427; 548/577
[58] Field of Search .................. 548/427; 514/411

[56] References Cited

U.S. PATENT DOCUMENTS

| 4,595,688 | 6/1986 | Maryanoff | 514/285 |
| 4,678,791 | 7/1987 | Napier | 514/290 |
| 4,719,216 | 1/1988 | Maryanoff | 514/292 |

FOREIGN PATENT DOCUMENTS 130069  1/1985 European Pat. Off. .
201085 11/1986 European Pat. Off. .

Primary Examiner—Mark L. Berch
Attorney, Agent, or Firm—Oblon, Spivak, McClelland, Maier & Neustadt

[57] ABSTRACT

A 5-phenyl-1,3,3a,4,5,9b-hexahydro-3H-benz(e)indole compound of the formula I:

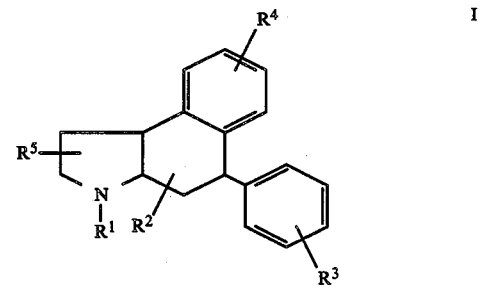

wherein $R^1$ is hydrogen or $C_{1-6}$ alkyl, $R^2$ is hydrogen or $C_{1-3}$ alkyl in the 3a- or 4-position, $R^3$ and $R^4$ are each hydrogen, hydroxyl, halogen, $C_{1-3}$ alkyl, $C_{1-3}$ alkoxy, $C_{1-3}$ alkylthio or trifluoromethyl, acetylamino or amino and $R^5$ is hydrogen or $C_{1-3}$ alkyl, or a salt thereof with a physiologically tolerated acid. The compounds and compositions are useful for treating depression or treating convulsions and which exhibit a sedative and tranquilizing effect when administered to a patient.

13 Claims, No Drawings

5-PHENYL-1,2,3A,4,5,9B-HEXAHYDRO-3H-BENZ-(E)INDOTES PREPARATION AND USE THEREOF AS DRUGS

The present invention provides novel 5-phenyl-1,2,3a,4,5,9b-hexahydro-3H-benz[e]indoles, processes for preparing the same, therapeutic compositions containing same, and the use thereof in the treatment of disorders.

The prior art discloses tricyclic pyrrolo[2,1-a]isoquinoline derivatives and phenylbenz[h]isoquinoline derivatives which are said to have antidepressive activity [European Laid-Open Applications 130,069 and 201,085].

We have now found that 5-phenyl-1,2,3a,4,5,9b-hexahydro-3H-benz[e]indoles of the formula I

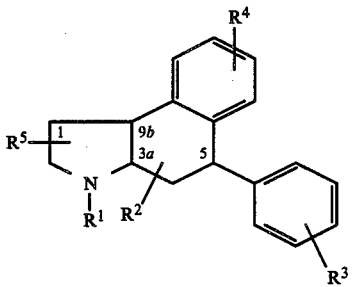

where $R^1$ is hydrogen or $C_{1-6}$-alkyl, $R^2$ is hydrogen of $C_{1-3}$-alkyl in the 3a- or 4-position, $R^3$ and $R^4$ are each hydrogen, hydroxyl, halogen, $C_{1-3}$-alkyl, $C_{1-3}$-alkoxy, $C_{1-3}$-alkylthio or trifluoromethyl, acetylamino or amino and $R^5$ is hydrogen or $C_{1-3}$-alkyl, and salts thereof with physiologically tolerated acids have useful pharmacological properties.

Particularly high utility is possessed by those compounds where $R^1$ is hydrogen or preferably methyl, ethyl or n-propyl, $R^2$, $R^4$ and $R^5$ are each hydrogen and $R^3$ is fluorine, chlorine, trifluoromethyl, methoxy, methylthio, methyl, hydroxyl, acetylamino, amino or in particular hydrogen.

It is to be noted that the compounds according to the invention have not less than 3 chiral centers in positions 3a, 5 and 9a and therefore appear as different diastereoisomers which can be separated for example by fractional crystallization. Of these compounds, compounds Ia, which are fused in the cis position on the pyrrolidine, prove to be particularly effective:

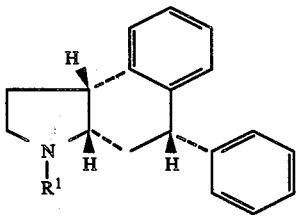

Specific examples are the following compounds: (±)-3aS(R), 5S(R), 9bR(S)-3-methyl-5-phenyl-1,2,3a,4,5,9b-hexahydro-3H-benz[e]indole, (+)-3aS,5S,9bR-3-methyl-5-phenyl-1,2,3a,4,5,9b-hexahydro-3H-benz[e]indole, (±)-3aS(R),5S(R),9bR(S)-3-ethyl-5-phenyl-1,2,3a,4,5,9b-hexahydro-3H-benz[e]indole and (±)-3aS(R),5S(R),9bR(S)-3-n-propyl-5-phenyl-1,2,3a,4,5,9b-hexahydro-3H-benz[e]indole.

The individual diastereoisomers can be separated into their antipodes via the salts with chiral carboxylic acids by a conventional method for resolving racemates.

The absolute configuration of the chiral centers in I can be determined by means of X-ray structural analysis.

The compounds of the formula I are preparable by (a) cyclizing a 3-phenyl-2-styrylpyrrolidine of the formula II

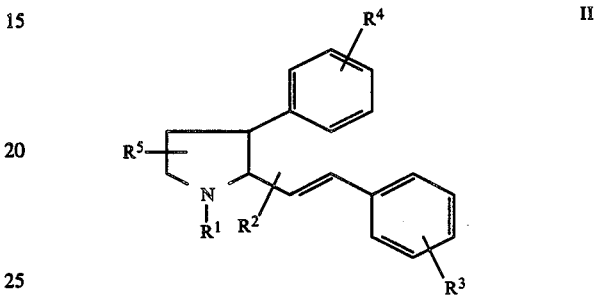

where $R^1$–$R^5$ are each as defined in claim 1, in the presence of a strong acid or (b) reducing a compound of the formula III

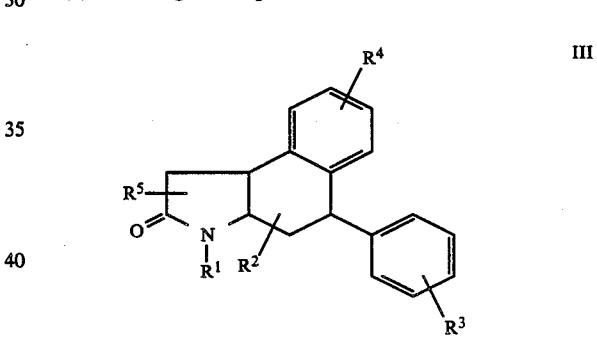

where $R^1$–$R^5$ reads as defined above, and subsequently, if desired, converting into their salts with physiologically tolerated acids.

The substituent $R^2$, in conformity with the formula I, is in the compounds of the formula II either on C-2 of the pyrrolidine ring or on the carbon atom of the styrene radical attached thereto.

Suitable acids for the cyclization reaction (a) are strong mineral acids, such as hydrochloric acid, phosphoric acid and in particular polyphosphoric acid and concentrated sulfuric acid. Conveniently, the acid is also used as the solvent. The cyclization takes plces at from 0° to 50° C. and is generally complete within from 1 to 10 hours.

If a cis-3-phenyl-2-styrylpyrrolidine derivative IIa is used in this cyclization reaction, the product obtained selectively comprises the particularly effective diastereoisomers Ia featuring cis-pyrrolidine fusion. If in addition the double bond in the cis-pyrrolidine derivative IIa is present in the more stable trans configuration, this method constitutes a way of selectively obtaining the active 3AS(R),5S(R),9bR(S) series.

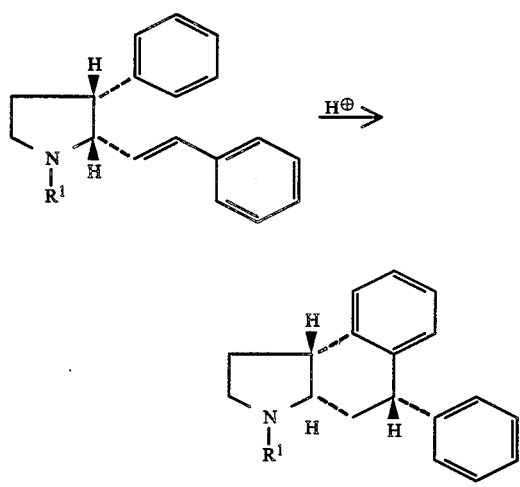

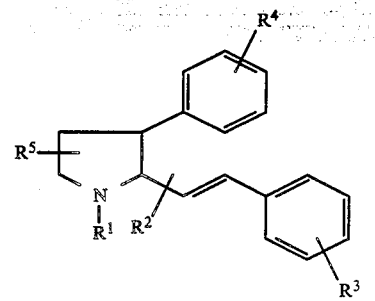

The reduction of compounds III is carried out with complex metal hydrides, for example lithium aluminum hydride, in an inert solvent, preferably in tetrahydrofuran, at from 0° to 80° C.

The compounds of the formula I are obtained in the majority of cases in the form of crystals and can be purified by recrystallization from customary organic solvents, preferably from a low alcohol, such as ethanol, or a low ester, preferably ethyl acetate, or by column chromatography.

Any mixtures obtained of diastereoisomers of the formula I can be separated into the pure diastereoisomers showing cis or trans fusion on the pyrrolidine, preferably by fractional crystallization from a lower alcohol.

The pure diastereoisomers can be resolved into the corresponding antipodes in a conventional manner, for example by forming diastereoisomeric salts with the aid of optically active acids. For example, the free base of the formula I is dissolved in a lower alcohol and one equivalent of (+)-or (−)-tartaric acid, (+)- or (−)-dibenzoyltartaric acid or (+)- or (−)-di-p-toluoyltartaric acid is added. Fractional crystallization then first gives the less soluble of the two diastereoisomeric salts, which is recrystallized until a constant angle of rotation is obtained. Freeing the free base gives the enantiomerically pure form of compound I.

The starting compounds of the formula II are preparable by reacting cinnamaldehyde or benzal acetone or derivatives thereof with monoalkylamines and hydrogen in the presence of hydrogenation catalysts:

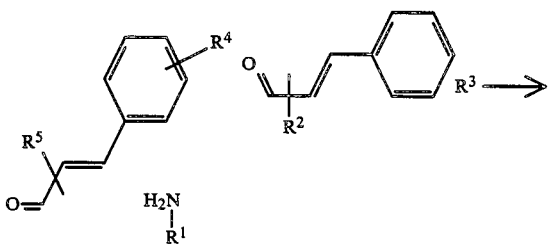

The reaction is carried out in an autoclave at from 70° to 150° C. The autoclave is charged with the catalyst in the form of a suspension in a solvent, followed by the monoalkylamine after the air has been displaced. After the reaction temperature has been attained, hydrogen is injected and the unsaturated carbonyl compound is pumped into the reaction space.

After the theoretically calculated amount of hydrogen has been taken up, excess amine is removed, the catalyst is filtered off with suction, and the reaction mixture is subjected to a fractional distillation which, in the high-boiling range, gives the desired compound II, generally in the form of a diastereoisomer mixture.

The catalyst use for the reaction of the $\alpha,\beta$-unsaturated carbonyl compounds was Raney cobalt whose reactivity had been reduced by storage for 200–600 hours in water at from 70° to 90° C. If the deactivation of the catalyst is overdone, the hydrogenation gives primarily high-boiling condensation products. An overactive catalyst gives in particular the regular reaction products of aminating hydrogenation.

The starting compounds of the formula II are also preparable from 1-alkyl-4-phenyl-5-formylpyrrolidin-2-one derivatives (German Laid-Open Applications DOS 3,537,075, DOS 3,624,102 and DOS 3,632,589) by Wittig reaction with benzylphosphonium salts or benzyl phosphonates in the presence of bases with or without subsequent reduction with complex metal hydrides, for example lithium aluminum hydride, in an inert organic solvent, preferably in tetrahydrofuran, at from 0° to 80° C. The same applies to the preparation of the starting compounds of the formula III, in which case the Wittig reaction is followed by the acid-catalyzed cyclization.

The free 5-phenyl-1,2,3a,4,5,9b-hexahydro-3H-benz-[e]indoles of the formula I can be converted in a conventional manner into the acid addition salt of a pharmacologically tolerated acid, preferably by treating a solution with an equivalent of the corresponding acid. Pharmaceutically tolerated acids are for example hydrochloric acid, phosphoric acid, sulfuric acid, methanesulfonic acid, sulfamic acid, maleic acid, fumaric acid, oxalic acid, tartaric acid and citric acid.

The compounds according to the invention have useful pharmacological properties. They are suitable for example for treating psychic disorders, in particular depressions, and also as sedatives and tranquilizers and surprisingly, owing to anticonvulsive activity, also for treating convulsive disorders.

The antidepressive activity of the substances according to the invention was studied using the following model:

2.15 mg/kg of reserpine administered subcutaneously to male mice (NMRI strain) having a weight of 20–26 g lowers the body temperature by 3° C. on average, measured 2 hours after the administration of reserpine and at an ambient temperature of 20°-22° C. Antidepressant substances inhibit this hypothermic effect, the degree of inhibition depending on the dose. The test substances were administered orally 60 minutes before the reserpine was administered.

The dose which inhibits reserpine-inducd hypothermia by 50%, ie. ED 50, is determined from the linear regression between log dose (mg/kg) and the relative decrease in the hypothermic effect.

The anticonvulsive action was measured on female mice (NMRI strain) having a weight of 22-26 g. Tonic spasms were induced by electroshock via ear electrodes. Stimulus data: a series of square-wave pulses 4.64 ms in duration and 14.7 mA in amplitude; frequency 100 Hz; duration of series 0.2 sec.

The electroshock was administered 60 minutes after the oral administration of the test compounds, and the appearance of tonic spasms was counted. n/dose=8. The ratios between the effectiveness (% protected animals) and log dose were calculated by probit analysis. ED 50 is the dose which inhibits the tonic spsms in 50% of the animals.

The ED 50 values (Table 1) of the compounds according to the invention are predominantly below the ED 50 value determined for imipramine, a standard antidepressant; the substances are thus more effective than the comparative substance. In some cases, the effectiveness is appreciably higher than that of imipramine (for example No. 1 or 4, by a factor of about 45).

Furthermore, the substances have anticonvulsive properties (Table 2). The effectivness of phenytoin, a clinically proven antiepileptic, is equalled or substantially exceeded (Examples 1 and 6).

The combination of antidepressive with anticonvulsive properties represents a novel combination of activities, since prior art tricyclic antidepressants are not anticonvulsive but can have a convulsion-reinforcing action.

TABLE 1

| Substance of Example No. | Antidepressive action ED 50 mg/kg, oral |
|---|---|
| 1 | 0.082 |
| 2 | 5.01 |
| 4 | 0.087 |
| 5 | 0.14 |
| 6 | 1.61 |
| 7 | 0.26 |
| imipramine | 3.82 |

TABLE 2

| Substance of Example No. | Anticonvulsive action ED 50 mg/kg, oral |
|---|---|
| 1 | 1.1 |
| 4 | ~46.4 |
| 5 | ~100 |
| 6 | 8.81 |
| 7 | 11.9 |
| phenytoin | 14.3 |

The invention accordingly also provides a therapeutic agent which contains a compound of the formula I or a pharmacologically tolerated acid addition salt thereof, as an active substance, as well as customary carriers and diluents, and also a method of using the novel compounds in the treatment of disorders.

The compounds according to the invention can be administered in a conventional manner orally or parenterally, intravenously or intramuscularly.

The dose depends on the age, state and weight of the patient and on the route of administration. In general, the daily dose of active substance ranges from about 1 to 20 mg/kg of weight in the case of oral administration and from 0.1 to 2 mg/kg of weight in the case of parenteral administration.

The novel compounds can be employed in the conventional solid or liquid pharmaceutical forms, such as tablets, film tablets, coated tablets capsules, powders, granules, suppositories, fusions, salves, creams or sprays. These are prepared in a conventional manner, and to do so the active substances can be mixed with conventional pharmaceutical auxiliaries such as tablet binders, fillers, preservatives, disintegrants, glidants, emollients, wetting agents, dispersants, emulsifiers, solvents, retardants, antioxidants and/or propellant gases (cf. H. Sucker et al.: Pharmazeutische Technologie, Thieme-Verlag, Stuttgart, 1978). The application forms thus obtained normally contain the active substance in an amount of from 0.1 to 99% by weight.

The Examples which follow illustrate the invention.

A. PREPARATION OF STARTING MATERIALS (a) 3-Phenyl-2-trans-styryl-N-methylpyrrolidine A 10 l stirred autoclave was charged with 1.4 kg of monomethylamine, 1.6 kg of ethanol and 0.1 kg of Raney cobalt. The autoclave was heated to 100° C. and charged with hydrogen under a pressure of 150 bar. 1.6 kg of cinnamaldehyde was pumped in over 10 hours. After the uptake of hydrogen had ceased, the reaction mixture was cooled down, filtered and subjected to fractional distillation. The fraction which came over at 153°-184° C./2 mbar contained 99.5 g of cis-3-phenyl-2-trans-styryl-N-methylpyrrolidine and 68.5 g of trans-3-phenyl-2-trans-styryl-N-methylpyrrolidine.

The mixture of diastereoisomers thus obtained was separated by fractional distillation through a packed column containing a stainless steel wire mesh helix (length 160 cm). The cis diastereoisomer passed over at 157° C./2 mbar and was more than 95% pure, while the trans diastereoisomer passed over at 160°-161° C./2 mbar and was more than 90% pure.

On standing, the trans diastereoisomer crystallizes out and can be recrystallized from ethyl acetate or n-octane; melting point: 63°-64° C.

(b) 3-Phenyl-2-trans-styryl-N-ethylpyrrolidine

In a 10 l autoclave, 2.0 kg of cinnamaldehyde were reacted with 1.4 kg of ethylamine at 90° C. under a hydrogen pressure of 150 bar in the presence of 100 g of Raney cobalt in 1.6 kg of ethanol. The cinnamaldehyde was added over 10 hours. After addition of cinnamaldehyde the reaction conditions were maintained for a further 6 hours.

The reaction mixture was subsequently subjected to fractional distillation. A fraction obtained at 160°-165° C./2 mbar contained 141 g of cis- and 161 g of trans-3-phenyl-2-trans-styryl-N-ethylpyrrolidine.

(c) 3-Phenyl-2-trans-styryl-N-n-propylpyrrolidine

In a 10 l autoclave, 2 kg of cinnamaldehyde were reacted with 1.6 kg of n-propylamine at 90° C. under a hydrogen pressure of 150 bar in the presence of 100 g of Raney cobalt. The cinnamaldehyde was added over 10 hours. The reaction mixture was subjected to fractional distillation. The fraction passing over at 150°–175° C./mbar was subjected to a fractional distillation as described in a) giving at 164°–166° C./2 mbar 130 g of cis-3-phenyl-2-trans-styryl-N-n-propylpyrrolidine (85% pure) and at 167°–168° C./2 mbar 145 g of trans-3-phenyl-2-trans-styryl-N-n-propylpyrrolidine (94% pure).

The same method was used to prepare the substituted 3-phenyl-2-trans-styrylpyrrolidine derivatives of the formula II by using substituted cinnamaldehyde or benzalacetone derivatives in the aminating hydrogenation.

(d)
cis-1-Methyl-4-phenyl-5-m-chlorostyrylpyrrolidin-2-one 32.8 g (77 mmol) of n-butyllithium (15% in hexane) were added dropwise under nitrogen with ice cooling to 36.0 g (77 mmol) of triphenyl-m-chlorobenzylphosphonium bromide in 150 ml of toluene in the course of 20 minutes, and the orange suspension was subsequently stirred for 15 minutes. 15.6 g (77 mmol) of cis-5-formyl-1-methyl-4- phenylpyrrolidin-2-one (German Laid-Open Application DOS 3,537,075 and 3,632,589; J. Org. Chem. 52 (1987), 4352) in 120 ml of toluene were then added dropwise and stirred in at room temperature for 3 hours (color change toward pale yellow). 200 ml of $H_2O$ were then added, the mixture was acidified with dilute HCL and filtered with suction, the phases were separated, the aqueous phase was extracted twice more with toluene, and the combined organic phases were washed with $H_2O$, dried and concentrated. The crude product was taken up in 100 ml of methyl t-butyl ether and filtered with suction and cooling to remove precipitated triphenylphosphine oxide. The filtrate was concentrated and purified by column chromatography (silica gel, eluent: 98/2 methylene chloride/methanol); yield: 16.1 g (67%). Judging by a $^1$H-NMR spectrum, the styryl side chain is 90% in the trans configuration and 10% in the cis configuration.

On using derivatives of 5-formyl-1-methyl-4-phenylpyrrolidin-2-one derivatives which are substituted on the benzene ring, a similar procedure produces the corresponding compounds substituted on the 4-phenyl ring (German Laid-Open Application DOS 3,537,075 and DOS 3,632,589, J. Org. Chem. 52 (1987), 4352).

(e)
cis-1-Methyl-3-phenyl-2-trans-m-chlorostyrylpyrrolidine

A solution of 3.0 g (9.6 mmol) of cis-1-methyl-4-phenyl-5-m-chlorostyrylpyrrolidin-2-one in 40 ml of ether was added dropwise at from 0° to 5° C. under nitrogen to 0.65 g (17 mmol) of lithium aluminum hydride and 30 ml of ether, and the mixture was subsequently stirred for 1 hour with ice cooling. 10% strength sodium hydroxide solution was then slowly added dropwise with cooling until the precipitate formed a conglomerate on the walls of the vessel. The supernatant ether phase was washed with $H_2O$ (pH 10), dried and concentrated. Purification by column chromatography (silica gel, eluent: 95/5 methylene chloride/methanol) gave the free base (2.3 g, 80%). This base was taken up in ethyl acetate and converted with ethereal HCl into the hydrochloride; melting point: 53°–56° C. B. Preparation of end products

EXAMPLE 1

(±)-3aS(R),5S(R),9bR(S)-3-Methyl-5-phenyl-1,2,3a,4,5,9b-hexahydro-3H -benz[e]indole hydrochloride 100.0 g (380 mmol) of cis-3-phenyl-2-trans-styryl-N-methylpyrrolidine in 235 ml of methylene chloride were slowly added dropwise at from 0° to 5° C. to a thoroughly stirred mixture of 108 ml of concentrated sulfuric acid and 493 ml of methylene chloride. The batch was subsequently stirred at from 0° to 5° C. for 1 hour and then at room temperature overnight. The workup comprised pouring onto 2.5 l of ice/water, adjusting to pH 8 with 10 percent sodium hydroxide solution, separating off the organic phase and extracting the aqueous phase a further three times with methylene chloride. The combined organic phases were washed with water, dried and concentrated. The residue was taken up in diisopropyl ether, the insoluble impurities were filtered off, and the filtrate was concentrated to dryness.

The 96.2 g of oil remaining were dissolved in 200 ml of ethanol and converted with ethereal hydrochloric acid into the hydrochloride, and the solution was concentrated to 150 ml and then admixed with ether to the onset of cloudiness. The slightly hygroscopic crystals formed overnight were filtered off with suction under nitrogen and dried under reduced pressure.

The mother liquor was concentrated to half its original volume and again admixed with ether until the onset of cloudiness, and the crystals were filtered off with suction. By repeating this operation twice more and combining the crystals a total of 83.5 g (74%) were isolated of a product having a melting point of 222°–223° C.

X-Ray structural analysis indicated in a 3aS(R), 5S(R),9bR(S) configuration for the chiral centers (cis-pyrrolidine fusion).

For conversion to the free base compound the hydrochloride was suspended in water, and the suspension was made alkaline with sodium hydroxide solution and extracted with methylene chloride. Melting point of the free base: 63°–64° C.

EXAMPLE 2

(±)-3aR(S),5R(S),9bR(S)-3-Methyl-5-phenyl-1,2,3a,4,5,9b-hexahydro-3H-benz[e]indole The synthesis was carried out similarly to Example 1 using trans-3-phenyl-2-trans-styryl-N-methylpyrrolidine. The crude product remaining on concentrating the organic phase was recrystallized as the free base from diisopropyl ether. Yield: 71%, colorless needles, melting point 96°–98° C.

X-Ray structural analysis revealed a 3aR(S),5R(S), 9bR(S) configuration for the chiral centers (transpyrrolidine fusion).

EXAMPLE 3

(±)-3aS(R),5S(R),9bR(S)-3-Methyl-5-phenyl-1,2,3a,4,5,9b-hexahydro-3H-benz[e]indole hydrochloride and diastereoisomer thereof The synthesis was carried out similarly to Example 2 using cis,trans-3-phenyl-2-trans-styryl-N-methylpyrrolidine. Crystallization of the crude product from diisopropyl ether gave as the less soluble fraction a virtually pure (±)-3aR(S),5R(S),9bR(S)-3-methyl-5-phenyl- 1,2,3a,4,5,9b-hexahydro-3H-benz[e]indole (cf. Example 2); melting point 94°–96° C.

The mother liquor was admixed with ethereal hydrochloric acid until no further precipitate was produced. The reaction mixture was heated to 30°–40° C. and admixed with ethanol until a clear solution had formed. Ether was then added until the onset of slight cloudiness. Cooling down the mixture gave crystals of (±)-3aS(R),5S(R),9bR(S)-3-methyl-5-phenyl-1,2,3a,4,5,9b-hexahydro-3H-benz[e]indole hydrochloride; melting point 49°–51° C.

EXAMPLE 4

(+)-3aS,5S,9bR-3-Methyl-5-phenyl-1,2,3a,4,5,9b-hexahydro-3H-benzo[e]indole 20.0 g (76 mmol) of (±)-3aS(R),5S(R),9bR(S)-3-methyl-5-phenyl-1,2,3a,4,5,9b-hexahydro-3H-benz[e]indole (cf. Example 1) in 300 ml of ethanol were admixed with a solution of 29.4 g (76 mmol) of (−)-di-O-p-toluoyl-L-tartaric acid in 300 ml of ethanol. The crystals formed overnight were filtered off with suction and washed with ethanol and then recrystallized twice from ethanol; $[\alpha]_D = -6.9°$ (DMF, c=1.007). To convert the salt into the optically pure free base, the salt was partitioned between methylene chloride and 10% strength sodium hydroxide solution. Customary working up and recrystallization from ethanol gave 7.8 g (39%) of (+)-3aS,5S,9bR-3-methyl-5-phenyl-1,2,3a,4,5,9b-hexahydro-3H-benz[e]indole, $[\alpha]_D = +58.3°$ (ethanol, c=0.980), melting point 92° C. X-Ray structural analysis confirmed the stated configuration. Melting point of hydrochloride: 238°–240° C.

The procedure of Examples 1 to 3 was used to prepare:

5. (±)-3aS(R),5S(R),9bR(S)-3-ethyl-5-phenyl-1,2,3a,4,5,9b-hexahydro-3H-benz[e]indole hydrochloride, melting point 237°–239° C. (starting material: cis-3-phenyl-2-trans-styryl-N-ethylpyrrolidine), 6. (±)-3aR(S),5R(S),9bR(S)-3-Ethyl-5-phenyl-1,2,3a,4,5,9b-hexahydro-3H-benz[e]indole hydrochloride, melting point 234°–236° C. (starting material: trans-3-phenyl-2-trans-styryl-N-ethylpyrrolidine), 7. (±)-3aS(R),5S(R),9bR(S)-3-n-propyl-5-phenyl-1,2,3a,4,5,9b-hexahydro-3H-benz[e]indole hydrochloride, melting point 255°–257° C. (starting material: cis-3-phenyl-2-trans-styryl-N-n-propylpyrrolidine), 8. (+)-3aR(S),5R(S),9bR(S)-3-n-propyl-5-phenyl-1,2,3a,4,5,9b-hexahydro-3H-benz[e]indole hydrochloride, melting point >275° C. (starting material: trans-3-phenyl-2-trans-styryl-N-n-propylpyrrolidine).

EXAMPLE 9

(±)-2,3,3a-Trimethyl-5-phenyl-1,2,3a,4,5,9b-hexahydro-3H-benz[e]indole hydrochloride 3.5 g (12.0 mmol) of 1,2,5-trimethyl-3-phenyl-2-trans-styrylpyrrolidine in 10 ml of methylene chloride were added dropwise to a thoroughly stirred mixture of 4.5 ml of concentrated sulfuric acid and 20 ml of methylene chloride at from 0° to 5° C. The batch was then stirred at from 0° to 5° C. for 1 hour and subsequently at room temperature overnight. The workup comprised pouring onto 300 ml of ice/water, adjusting to pH 8 with 10% strength sodium hydroxide solution, separating off the organic phase and extracting the aqueous phase three more times with methylene chloride. The combined organic phases were washed with water, dried and concentrated.

The removal of two diastereoisomers by column chromatography (silica gel, 95/5 methylene chloride/methanol) gave an apolar and a polar fraction which were each dissolved in ether, filtered and admixed with excess ethereal hydrochloric acid. The colorless solids precipitated after stirring for 15 minutes were filtered off with suction under nitrogen in the cold and dried in a vacuum drying cabinet.

The two diastereoisomeric hydrochlorides were isolated in a yield of 1.6 and 0.5 g respectively (41 and 13% respectively) and had melting ranges of 252°–254° C. and 264°–266° C. respectively.

The procedure of Example 9 was used to prepare:

10. (±)-1,3,4-trimethyl-5-phenyl-1,2,3a,4,5,9b-hexahydro-3H-benz[e]indole hydrochloride (starting material: 1,4-dimethyl-3-phenyl-2-trans-β-methylstyrylpyrrolidine), 11. (±)-1,4-Dimethyl-3-ethyl-5-phenyl-1,2,3a,4,5,9b-hexahydro-3H-benz[e]indole hydrochloride, melting point 243°–246° C.

12. (±)-2,3a-Dimethyl-3-ethyl-5-phenyl-1,2,3a,4,5,9b-hexahydro-3H-benz[e]indole hydrochloride, melting point 187°–190° C.

13. (+)-7-chloro-3-methyl-5-phenyl-1,2,3a,4,5,9b-hexahydro-3H-benz[e]indole hydrochloride 14. (+)-7-chloro-3-ethyl-5-phenyl-1,2,3a,4,5,9b-hexahydro-3H-benz[e]indole hydrochloride

15a (+)-3aS(R),5S(R),9bR(S)-3-methyl-5-m-chlorophenyl-1,2,3a,4,5,9b-hexahydro-3H-benz[e]indol-2-one 7.5 g (24 mmol) of cis-1-methyl-4-phenyl-5-m-chlorostyrylpyrrolidin-2-one in 70 g of polyphosphoric acid were stirred at 100° C. for 1 hour. The batch was subsequently poured onto 0.5 l of ice-water, and the mixture was made alkaline with concentrated sodium hydroxide solution, and the aqueous phase was extracted twice with methylene chloride. The combined organic phases were washed with water, dried and concentrated. The residue was dissolved in a little ethyl acetate, three times the volume of cyclohexane was added, and crystals were produced by cooling. The crystals were filtered off with suction, washed with cyclohexane and dried under reduced pressure. This gave 5.9 g (79%); melting point: 147°–148° C.

15b (±)-3aS(R),5S(R),9bR(S)-3-Methyl-5-m-chlorophenyl-1,2,3a,4,5,9b-hexahydro-3H-benz[e]indole hydrochloride A solution of 3.8 g (12 mmol) of (±)-3aS(R),5S(R),9bR(S)-3-methyl-5-m-chlorophenyl-1,2,3a,4,5,9b-hexahydro-3H-benz[e]indol-2-one in 80 ml of tetrahydrofuran was added dropwise at from 0° to 5° C. under nitrogen to 1.78 g (47 mmol) of lithium aluminum hydride in 20 ml of tetrahydrofuran, and the mixture was stirred with refluxing for 3 hours. 10% strength sodium hydroxide solution was then slowly added dropwise with cooling until the precipitate formed conglomerated on the walls of the vessel. The precipitate was filtered off with suction, and the organic phase was washed with water (pH 10), dried and concentrated. The yellow oil remaining was taken up in 120 ml of ether, admixed with ethereal hydrochloric acid with cooling under nitrogen, the precipitated solids were filtered off with suction under nitrogen and washed thoroughly with ether, and the product was dried in a vacuum drying cabinet. This gave 3.4 g (85%); melting point: 75°-78° C.

The procedure of Example 15 was followed to prepare:

16. (+)-3aS(R),5S(R),9bR(S)-3-methyl-5-p-chlorophenyl-1,2,3a,4,5,9b-hexahydro-3H-benz[e]indole hydrochloride
17. (+)-3aS(R),5S(R),9bR(S)-3-methyl-5-p-methylphenyl-1,2,3a,4,5,9b-hexahydro-3H-benz[e]indole hydrochloride
18. (±)-3aS(R),5S(R),9bR(S)-3-methyl-5-m-methoxyphenyl-1,2,3a,4,5,9b-hexahydro-3H-benz[e]indole hydrochloride
19. (±)-3aS(R),5S(R),9bR(S)-3-methyl-5-p-trifluoromethylphenyl-1,2,3a,4,5,9b-hexahydro-3H-benz[e]indole hydrochloride
20. (±)-3aS(R),5S(R),9bR(S)-3-methyl-5-m-chlorophenyl-1,2,3a,4,5,9b-hexahydro-3H-benz[e]indole hydrochloride
21. (+)-3aS(R),5S(R),9bR(S)-3-methyl-5-m-fluorophenyl-1,2,3a,4,5,9b-hexahydro-3H-benz[e]indole hydrochloride
22. (±)-3aS(R),5S(R),9bR(S)-3-methyl-5-o-chlorophenyl-1,2,3a,4,5,9b-hexahydro-3H-benz[e]indole hydrochloride
23. (±)-3aS(R),5S(R),9bR(S)-3-methyl-5-(2,4-dichlorophenyl)-1,2,3a,4,5,9b-hexahydro-3H-benz[e]indole hydrochloride
24. (±)-3aS(R),5S(R),9bR(S)-3-methyl-5-p-fluorophenyl-1,2,3a,4,5,9b-hexahydro-3H-benz[e]indole hydrochloride
25. (±)-3aS(R),5S(R),9bR(S)-3-methyl-5-m-methylphenyl-1,2,3a,4,5,9b-hexahydro-3H-benz[e]indole hydrochloride
26. (±)-3aS(R),5S(R),9bR(S)-3-methyl-5-o-fluorophenyl-1,2,3a,4,5,9b-hexahydro-3H-benz[e]indole hydrochloride.
27. (±)-3as(R),5S(R),9bR(S)-3-methyl-5-p-thiomethylphenyl-1,2,3a,4,5,9b-hexahydro-3H-benz[e]indole hydrochloride
28. (+)-3aS(R),5S(R),9bR(S)-3-methyl-5-p-methoxyphenyl-1,2,3a,4,5,9b-hexahydro-3H-benz[e]indole hydrochloride
29. (±)-3aS(R),5S(R),9bR(S)-3-methyl-5-p-hyroxyphenyl-1,2,3a,4,5,9b-hexahydro-3H-benz[e]indole hydrochloride (preparation from 28 by ether cleavage with boron tribromide in chloroform).
30. (±)-3aS(R),5S(R),9bR(S)-3-methyl-5-p-acetaminophenyl-1,2,3a,4,5,9b-hexahydro-3H-benz[e]indole hydrochloride
31. (±)-3aS(R),5S(R),9bR(S)-3-methyl-5-p-aminophenyl-1,2,3a,4,5,9b-hexahydro-3H-benz[e]indole hydrochloride

EXAMPLE 32

A tablet press was used to press tablets in a conventional manner from the following composition:
12.5 mg of substance of Example 1
120 mg of corn starch
13.5 mg of gelatin
45 mg of lactose
2.25 mg of Aerosil ® (chemically pure silica in submicroscopically fine division)
6.75 mg of potato starch (as 6% strength paste)

EXAMPLE 33

Coated tablets are prepared in a conventional manner from the following composition:

7.5 mg of substance of Example 5
60 mg of core material
60 mg of sugar-coated material The core material comprises 9 parts of corn starch, 3 parts of lactose and 1 part of Luviskol ® VA 64 (vinylpyrrolidone/vinyl acetate copolymer, 60:40; cf. Pharm. Ind. 1962, 586). The sugar-coating material comprises 5 parts of cane sugar, 2 parts of corn starch, 2 parts of calcium carbonate and 1 part of talc. The coated tablets thus prepared are then coated with an overcoat resistant to gastric juices.

EXAMPLE 34

1 g of substance of Example 7 is dissolved in 5000 ml of water in the presence of NaCl, and the solution is brought to pH 6.0 with 0.1N NaOH to give a blood isotonic solution. 5 ml each of this solution are introduced into ampoules and sterilized.

We claim:

1. A 5-phenyl-1,2,3a,4,5,9b-hexahydro-3H-benz[e]indole of compound the formula I:

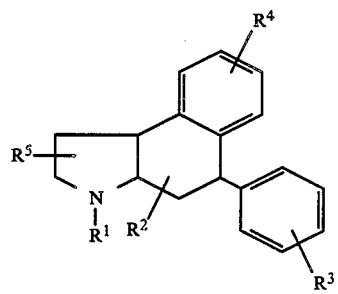

where $R^1$ is hydrogen or $C_{1-6}$-alkyl, $R^2$ is hydrogen or $C_{1-3}$-alkyl in the 3a- or 4-position, $R^3$ and $R^4$ are each hydrogen, hydroxyl, halogen, $C_{1-3}$-alkyl, $C_{1-3}$-alkoxy, $C_{1-3}$-alkylthio or trifluoromethyl, acetylamino or amino and $R^5$ is hydrogen or $C_{1-3}$-alkyl, or a salt thereof with a physiologically tolerated acid.

2. The compound of the formula I as claimed in claim 1, where $R^1$ is hydrogen, methyl, ethyl or n-propyl, $R^2$, $R^4$ and $R^5$ are each hydrogen and $R^3$ is hydrogen, fluorine, chlorine, trifluoromethyl, methoxy, methylthio, methyl, hydroxyl, acetamino or amino.

3. (±)-3aS(R),5S(R),9bR(S)-3-Methyl-5-phenyl-1,2,3a,4,5,9b-hexahydro-3H-benz[e]indole.

4. (35 )-3aS,5S,9bR-3-Methyl-5-phenyl-1,2,3a,4,5,9b-hexahydro-3H-benz[e]indole.

5. (±)-3aS(R),5S(R),9bR(S)-3-Ethyl-5-phenyl-1,2,3a,4,5,9b-hexahydro-3H-benz[e]indole.

6. (±)-3aS(R),5S(R),9bR(S)-3-n-Propyl-5-phenyl-1,2,3a,4,5,9b-hexahydro-3H-benz[e]indole.

7. A pharmaceutical composition for treating depression or convulsive disorders in a patient or for imparting a sedative or tranqulizing effect to said patient, which comprises an effective amount of one or more compounds of claim 1 as an active substance and a pharmaceutically-acceptable carrier.

8. A method for treating depression or convulsive disorders in a patient or for imparting a sedative or tranquilizing effect to said patient, which comprises administering an effective amount of one or more compounds according to claim 1.

9. A method for treating depression or convulsive disorders in a patient or for imparting a sedative or tranquilizing effect to said patient, which comprises administering an effective amount of a pharmaceutical composition according to claim 7.

10. The method according to claim 8, wherein said effective amount is about 1 to 20 mg/kg of body weight for oral administration.

11. The method according to claim 8, wherein said effective amount is about 0.1 to 2 mg/kg of body weight for parenteral administration.

12. The method according to claim 9, wherein said effective amount is about 1 to 20 mg/kg of body weight for oral administration.

13. The method according to claim 9, wherein said effective amount is about 0.1 to 2 mg/kg of body weight for parenteral administration.

* * * * *

UNITED STATES PATENT AND TRADEMARK OFFICE
CERTIFICATE OF CORRECTION

PATENT NO. : 4,877,807
DATED : Oct. 31, 1989
INVENTOR(S) : Gerd Steiner, et al

It is certified that error appears in the above-identified patent and that said Letters Patent is hereby corrected as shown below:

In the Title: "Benz(e)indotes" should be replaced by
-- Benz(e)indoles,--

Signed and Sealed this

Twenty-fifth Day of December, 1990

Attest:

HARRY F. MANBECK, JR.

*Attesting Officer*     Commissioner of Patents and Trademarks